US00PP21317P3

(12) United States Plant Patent
Chandler

(10) Patent No.: US PP21,317 P3
(45) Date of Patent: Sep. 28, 2010

(54) STRAWBERRY PLANT NAMED 'FLORIDA ELYANA'

(50) Latin Name: ***Fragaria×ananassa* Duchesne**
Varietal Denomination: Florida Elyana

(75) Inventor: Craig Chandler, Tampa, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/214,519

(22) Filed: Jun. 20, 2008

(65) Prior Publication Data

US 2009/0320168 P1 Dec. 24, 2009

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner*—Susan B McCormick Ewoldt

(57) ABSTRACT

A new and distinct variety of strawberry (*Fragaria×ananassa*), which originated from seed produced by a hand-pollinated cross between FL 96-114 and FL 95-200. The new strawberry, named 'Florida Elyana', is distinguished by production of large, firm, exceptionally flavored fruit and resistance to crown and fruit rots when grown in west central Florida or other areas that have a subtropical climate similar to that of west central Florida.

2 Drawing Sheets

Botanical designation:

*Fragaria×ananassa* Duchesne

BACKGROUND OF THE NEW VARIETY

The present invention relates to a new and distinct variety of strawberry (*Fragaria×ananassa* Duchesne) plant that is named 'Florida Elyana' and more particularly to a strawberry plant that is distinguished by its production of large, firm, flavorful fruit from December through March in west central Florida, as well as its resistance to crown and fruit rots. Asexual propagation was performed at Dover, Fla. where the selection was made and plants were tested. Contrast is made to 'Strawberry Festival' (U.S. Plant Pat. No. 14,739), currently the dominant variety in Hillsborough County, Fla., for reliable description. This new variety is a promising candidate for commercial success because of its production of large, firm fruit.

ORIGIN OF THE VARIETY

This strawberry plant (genotype) originated in a strawberry breeding plot at Dover, Fla. The seed parent was FL 96-114 (not patented) and the pollen parent was FL 95-200 (not patented), both are proprietary breeding selections. FL 96-114 resulted from a cross between 'Sweet Charlie' (U.S. Plant Pat. No. 8,729) and 'Cuesta' (U.S. Plant Pat. No. 8,662). FL 95-2000 has a number of cultivars in its complex pedigree, including "Rosa Linda' (U.S. Plant Pat. No. 9,866), 'Irvine' (U.S. Plant Pat. No. 7,172), 'Pajaro' (U.S. Plant Pat. No. 4,538), and 'Dover' (not patented). The seeds resulting from the controlled hybridization were germinated in a greenhouse and the resulting seedlings were planted and allowed to produce daughter plants by asexual propagation (i.e. by runners). Two daughter plants from each seedling were transplanted to raised beds, where they fruited. 'Florida Elyana' strawberry (as represented by two daughter plants from the original seedling) exhibited attractive, firm fruit, and therefore was selected for further evaluation. 'Florida Elyana' was the 51st selection numbered in the 2000-01 stage 1 trial, and thus was designated FL 00-51. It has been asexually propagated by runners, annually, and further test plantings have established that the vegetative and fruit characteristics of the propagules are identical to the initial two daughter plants. 'Florida Elyana' has more consistently attractive fruit than either of its parents. Sometimes the primary fruit of the FL 96-114 are deformed, while the fruit of FL 95-200 can have a seedy appearance. Also, 'Florida Elyana' fruit has better flavor than the fruit of either of its parents. The firmness of 'Florida Elyana' fruit is softer than the fruit of FL 96-114, but firmer than the fruit of FL 95-200.

SUMMARY OF THE VARIETY

'Florida Elyana', when grown in a subtropical fall and winter climate, is set apart from all other strawberry plants by a combination of the following characteristics: ability to produce large, firm, exceptionally flavored fruit over a long harvest period; ease of harvest; and resistance to crown and fruit rots.

DETAILED BOTANICAL DESCRIPTION

Figure 1:
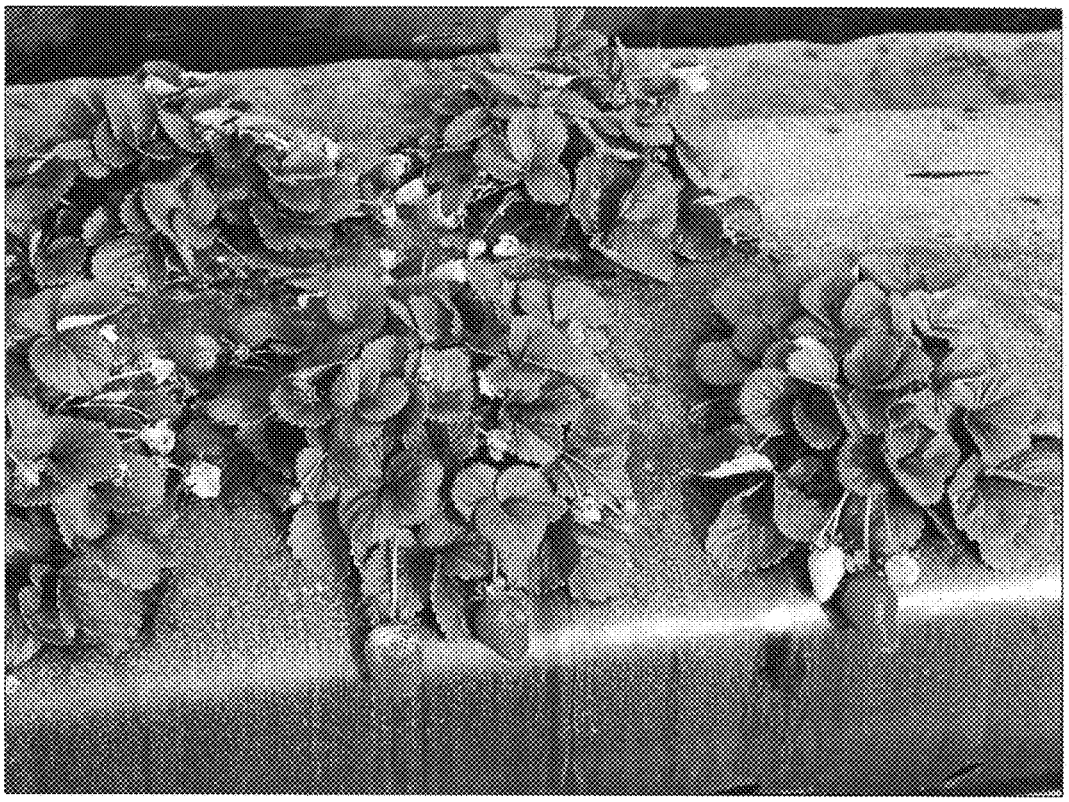
FIG. 1 shows a typical specimen of the plant of the 'Florida Elyana' strawberry.
Figure 2:
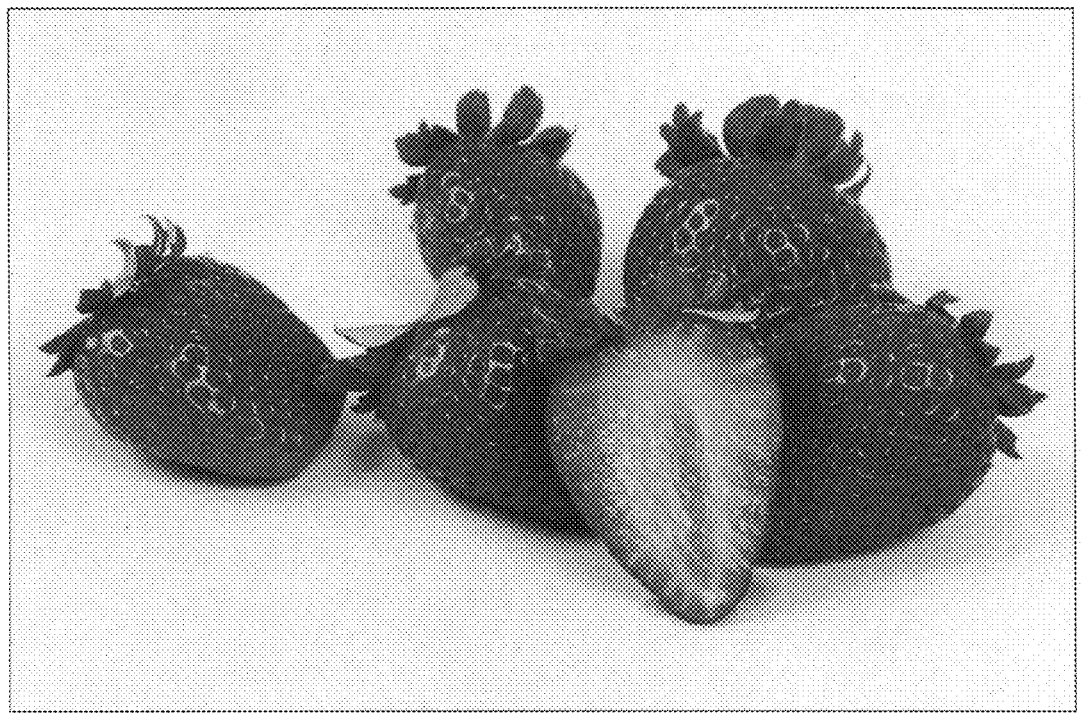
FIG. 2 shows a typical specimen of the fruit of the plant of the 'Florida Elyana' strawberry.

The following botanical description is that of mature (approximately five months old) plants of the variety grown under the ecological conditions (warm days, cool nights) prevailing at Balm, Fla. in March. Colors are described using a standard Royal Horticultural Society (RHS) Color Chart.

'Florida Elyana' is a short day cultivar. Average height and width for mature plants is 23 cm and 35 cm respectively. Average petiole length and diameter is 15.2 cm and 3.0 mm respectively, and petioles have a light to medium pubescence. The average number of leaflets per leave is 3. The average length and breadth of terminal leaflets is 75 and 63 mm respectively. The average length and breadth of secondary leaflets is 68 and 61 mm respectively. Leaflets have a netted venation pattern with the veins appearing slightly sunken when viewed from the upper surface. Leaflet margins are crenate and average 21 serrations per terminal leaflet, and 22 per secondary leaflet. The upper leaf surface is a dark grey green (RHS 139B); the lower leaf surface is a light grey green (RHS 139C); and the petiole is a medium yellow green (RHS 145A). The average length and diameter of petiolules is 8 and 2 mm respectively, and they are a medium yellow green (RHS 145A). Flowers open below the canopy, and have 6 petals and an average of 25 stamens. Individual petals are nearly circular, with a length of 9 mm and a width of 10 mm. Their apex and base are rounded, their margins are entire, and the color of their upper and lower surfaces are white (RHS 155C). The diameter of the corolla (i.e. the petals collectively) is 22 mm. Pedicels attached to mature primary fruit are 11.0 to 18.5 cm long, with branching of the inflorescence usually occurring very close to the crown. Mean fruit weight is greater than that of 'Strawberry Festival': 27 g vs. 21 g in 2004-05 and 24 g vs. 17 g in 2006-07 (Table 1 and 2). Primary fruit are mostly wedged shaped, often showing a longitudinal dimple on the broad sides of the fruit; whereas secondary and tertiary fruit are mostly medium conic. 'Florida Elyana' fruit are quite susceptible to surface cracking, which is due to exposure to free moisture. Thus we are not recommending this cultivar for open field culture where there is a high likelihood of multiple rain or dew events during the fruiting season. External fruit color is a bright orange red (RHS 34B), and internal color is light orange red (RHS 35A). Fruit have an internal cavity that averages 12 mm in length and 4 mm in width. There is an average of 258 achenes per fruit, and these achenes are positioned such that the top of the achenes are even with the fruit surface. The calyx is generally medium in size (2.0 to 4.8 cm in diameter) and attractive. Sepals are 9 to 20 mm long, 5 to 15 mm wide, and green (RHS 137A top; 138B bottom). Fruit texture is firm (Table 3), and the flavor is usually sweet with a pleasant aroma. The soluble solid content of 'Florida Elyana' fruit is as high as or higher than that of 'Strawberry Festival'. (Table 4), and its SSC/TA ratio is consistently higher than that of 'Strawberry Festival'. The preferred planting date for 'Florida Elyana' is Oct. 5th to October 15th. 'Florida Elyana' is as productive as 'Strawberry Festival' in December and January, but not as productive later in the season (Tables 1 and 2). This could be due to the fact that 'Florida Elyana' plants stay relatively small throughout the season, whereas 'Strawberry Festival' plants are more vigorous in terms of producing new branch crowns. Growers may be able to increase the productivity of 'Florida Elyana' on a per unit area basis by planting this cultivar at a higher than standard density. 'Florida Elyana' is resistant to the two most serious disease problems on strawberry in Florida: Botrytis fruit rot (caused by *Botrytis cinerea*) and anthracnose fruit rot (caused by *Colletotrichum acutatum*). In an unsprayed trial during the 2007-08 season, only 3% of the 'Florida Elyana' fruit harvested from mid February to mid March showed symptoms of anthracnose fruit rot, compared to 53% for 'Treasure' (U.S. Plant Pat. No. 12,414), the susceptible control. 'Florida Elyana' also appears to be resistant to Colletotrichum and Phytophthora crown rots. The susceptibility of 'Florida Elyana' to the twospotted spider mite (*Tetranychus urtricae* Koch) is unknown, but a serious infestation has not yet been observed in research center or commercial trials. Fruit of 'Florida Elyana' is intended to be used for the fresh market.

TABLE 1

Performance of strawberry cultivars at Dover, Fla. during the 2004-05 season[z].

| | Marketable yield (g/plant) | | | | | Wt/fruit[z] |
|---|---|---|---|---|---|---|
| Cultivar | December | January | February | March | Total | (g) |
| F. Elyana | 76 a[y] | 108 a | 178 a | 353 b | 715 b | 27.1 a |
| S. Festival | 37 b | 144 a | 155 a | 592 a | 928 a | 20.6 b |

[z]Mean fruit weight was determined by dividing total marketable fruit yield per plot by total marketable fruit number per plot.
[y]Means based on four replications of 10 plants each. Mean separation within columns by Fisher's protected LSD test, P ≦ 0.05.

TABLE 2

Performance of strawberry cultivars at Dover, Fla. during the 2006-07 season[z].

| | Marketable yield (g/plant) | | | | | Wt/fruit[z] |
|---|---|---|---|---|---|---|
| Cultivar | December | January | February | March | Total | (g) |
| F. Elyana | 46 a[y] | 99 a | 159 b | 322 b | 626 b | 24.4 a |
| S. Festival | 65 a | 94 a | 218 a | 459 a | 836 a | 17.3 b |

[z]Mean fruit weight was determined by dividing total marketable fruit yield per plot by total marketable fruit number per plot.
[y]Means based on four replications of 10 plants each. Mean separation within columns by Fisher's protected LSD test, P ≦ 0.05.

TABLE 3

Mean acceptance scores (9-point hedonic scale) for appearance, texture, and flavor of 'Florida Elyana' and 'Strawberry Festival' strawberry evaluated over two harvest seasons.

| | February 2006 | March 2006 | January 2007 | February 2007 | March 2007 |
|---|---|---|---|---|---|
| Appearance | | | | | |
| F. Elyana | 6.6 b[z] | 7.5 a | 5.9 a | 6.4 b | 6.0 a |
| S. Festival | 7.8 a | 6.8 b | 6.2 a | 7.2 a | 6.3 a |
| Texture | | | | | |
| F. Elyana | 7.4 a | 7.1 a | 6.9 a | 6.9 a | 6.2 a |
| S. Festival | 7.5 a | 6.6 a | 6.4 a | 6.8 a | 6.2 a |
| Flavor | | | | | |
| F. Elyana | 7.3 a | 7.0 a | 6.5 a | 6.7 a | 6.2 a |
| S. Festival | 7.3 a | 6.2 b | 5.9 b | 6.9 a | 5.1 b |

[z]Mean separation within columns by Fisher's protected LSD test, P ≦ 0 05.

TABLE 4

Soluble solid content (SSC) and titratable acidity (TA) of 'Florida Elyana' and 'Strawberry Festival' strawberry evaluated over two harvest seasons.

| | February 2006 | March 2006 | January 2007 | February 2007 | March 2007 |
|---|---|---|---|---|---|
| SSC (°Brix) | | | | | |
| F. Elyana | 10.2 a[z] | 8.2 a | 7.7 a | 9.6 a | 7.3 a |
| S. Festival | 7.5 b | 7.5 b | 6.9 b | 9.8 a | 6.2 b |
| TA (%) | | | | | |
| F. Elyana | 0.82 a | 0.58 a | 0.78 b | 0.71 b | 0.69 a |
| S. Festival | 0.75 b | 0.63 a | 0.91 a | 0.87 a | 0.73 a |

[z]Mean separation within columns by Fisher's protected LSD test, P ≦ 0.05.

We claim:

1. A new and distinct strawberry plant as illustrated and described, characterized by 1) resistance to crown and fruit rots, and 2) production of large, firm, exceptionally flavored fruit when grown in west central Florida.

* * * * *